United States Patent
Mojzych et al.

(10) Patent No.: US 12,319,699 B2
(45) Date of Patent: Jun. 3, 2025

(54) L-PROLINE SULFONAMIDE DERIVATIVES COMPRISING PYRAZOLO[4,3-E]TETRAZOLO[4,5-B][1,2,4]TRIAZINE SYSTEM, METHOD OF MANUFACTURING THEREOF, USES THEREOF AND PHARMACEUTICAL COMPOSITION COMPRISING THE SAME

(71) Applicants: UNIWERSYTET MEDYCZNY W BIALYMSTOKU, Bialystok (PL); UNIWERSYTET PRZYRODNICZO-HUMANISTYCZNY W SIEDLCACH, Siedlce (PL); UNIWERSYTET MEDYCZNY W LUBLINIE, Lublin (PL)

(72) Inventors: Mariusz Mojzych, Siedlce (PL); Katarzyna Kotwica-Mojzych, Lublin (PL); Anna Bielawska, Jurowce (PL); Krzysztof Bielawski, Jurowce (PL); Dariusz Pawlak, Bialystok (PL); Justyna Magdalena Hermanowicz, Bialystok (PL); Anna Tankiewicz-Kwedlo, Bialystok (PL); Anna Szymanowska, Szczuczyn (PL)

(73) Assignees: UNIWERSYTET MEDYCZNY W BIALYMSTOKU, Bialystok (PL); UNIWERSYTET PRZYRODNICZO-HUMANISTYCZNY W SIEDLCACH, Siedlce (PL); UNIWERSYTET MEDYCZNY W LUBLINIE, Lublin (PL)

( * ) Notice: Subject to any disclaimer, the term of this patent is extended or adjusted under 35 U.S.C. 154(b) by 999 days.

(21) Appl. No.: 17/298,088

(22) PCT Filed: Nov. 27, 2019

(86) PCT No.: PCT/PL2019/000110
§ 371 (c)(1),
(2) Date: May 28, 2021

(87) PCT Pub. No.: WO2020/111956
PCT Pub. Date: Jun. 4, 2020

(65) Prior Publication Data
US 2022/0017529 A1    Jan. 20, 2022

(30) Foreign Application Priority Data
Nov. 30, 2018   (PL) .......................... 427991

(51) Int. Cl.
*C07D 487/14*    (2006.01)
*A61P 35/00*    (2006.01)

(52) U.S. Cl.
CPC ............ *C07D 487/14* (2013.01); *A61P 35/00* (2018.01)

(58) Field of Classification Search
CPC ................................................... C07D 487/14
See application file for complete search history.

(56) References Cited

FOREIGN PATENT DOCUMENTS

| CA | 2956465 | 3/2016 |
|---|---|---|
| PL | 198966 | 4/2004 |
| PL | 408801 | 1/2016 |

OTHER PUBLICATIONS

Gornowicz et. al. (Int. Mol. Sci. 2022, 21, 5221) (Year: 2022).*
PCT Search Report and Written Opinion prepared for PCT/PL2019/000110, completed Mar. 6, 2020.
Polish Search Report prepared for Polish Patent Application No. P.427991, completed Sep. 5, 2019.
Mojzych, M., et al., "Synthesis and Structure of 7-methyl-5-phenyl-IH-pyrazolo[4,3-e]tetrazolo[4,5-b][1,2,4]triazine," 2005, Journal of Chemical Crystallography, vol. 35, No. 2, pp. 151-155.

(Continued)

*Primary Examiner* — John S Kenyon
*Assistant Examiner* — Rehana Ismail
(74) *Attorney, Agent, or Firm* — Barnes & Thornburg LLP

(57) ABSTRACT

The subject matter of the invention relates to novel sulfonamide derivatives of 7-methyl-5-phenyl-pyrazolo[4,3-c]tetrazolo[4,5-b] [1,2,4]triazine comprising L-proline or 4-hydroxy-L-proline in the sulfonamide group. The novel compounds exhibit cytostatic activity against gastric cancer cell (AGS) and colorectal cancer cell (DLD-1 and HT-29) lines and may be used as novel medicaments which have anticancer action. The subject matter of the invention also relates to a method of manufacturing such derivatives, as well as uses thereof and a pharmaceutical composition comprising the same.

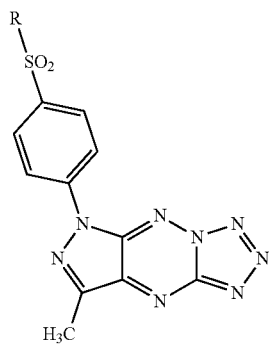

(Formula 1)

15 Claims, 11 Drawing Sheets

(56) References Cited

OTHER PUBLICATIONS

Mojzych, M., et al., "Valence tautomerism of new pyrazolo[4,3-e]tetrazole[4,5-b] [1,2,4]triazines," 2014, Journal of Molecular Structure, No. 1067, pp. 147-153.
Mojzych, M., "Cytotoxic Activity of Some Pyrazolo[4,3-e][1,2,4]Triazines Against Human Cancer Cell Lines," 2011, J. Chem. Soc.Pakistain, vol. 33, No. 1, pp. 123-128.

* cited by examiner

L-PROLINE SULFONAMIDE DERIVATIVES COMPRISING PYRAZOLO[4,3-E] TETRAZOLO[4,5-B][1,2,4]TRIAZINE SYSTEM, METHOD OF MANUFACTURING THEREOF, USES THEREOF AND PHARMACEUTICAL COMPOSITION COMPRISING THE SAME

CROSS-REFERENCE TO RELATED APPLICATIONS

This application is a national stage entry under 35 U.S.C. § 371 (b) of PCT International Application No. PCT/PL2019/000110, filed Nov. 27, 2019, which claims the benefit of Polish Patent Application Serial No. P.427991, filed on Nov. 30, 2018, the entire disclosures of both of which are incorporated herein by reference.

SUMMARY OF THE INVENTION

The subject matter of the invention relates to novel sulfonamide derivatives of 7-methyl-5-phenyl-pyrazolo[4,3-e]tetrazolo[4,5-b][1,2,4]triazine comprising L-proline methyl ester or 4-hydroxy-L-proline methyl ester in the sulfonamide group. These compounds exhibit anticancer, cytostatic, cytotoxic and antiproliferative action, in particular with respect to neoplastic cells, especially cancer cells of the alimentary track, such as gastric cancer cells and colorectal cancer cells. The subject matter of the present invention further relates to a method of manufacturing such novel sulfonamide derivatives of 7-methyl-5-phenyl-pyrazolo[4,3-e]tetrazolo[4,5-b][1,2,4]triazine comprising L-proline methyl ester or 4-hydroxy-L-proline methyl ester. The subject matter of the present invention also relates to uses of such novel sulfonamide derivatives of 7-methyl-5-phenyl-pyrazolo[4,3-e]tetrazolo[4,5-b][1,2,4]triazine comprising L-proline methyl ester or 4-hydroxy-L-proline methyl ester associated with their anticancer, cytostatic and/or cytotoxic activity, in particular with respect to neoplastic cells, especially gastric cancer cells and colorectal cancer cells, as well as a pharmaceutical composition comprising such sulfonamide derivatives of 7-methyl-5-phenyl-pyrazolo[4,3-e]tetrazolo[4,5-b][1,2,4]triazine comprising L-proline methyl ester or 4-hydroxy-L-proline methyl ester in the sulfonamide group.

The prior art discloses a derivate of 7-methyl-5-phenyl-pyrazolo[4,3-e]tetrazolo[4,5-b][1,2,4]triazine that exhibits anticancer activity as well as methods of synthesis thereof (Mojzych M., Chem. Soc. Pak., 2011, 33, 123-128; Mojzych M., Rykowski A., Heterocycles, 2004, 63, 1829-1838).

Patent No. PL-198966 and literature (Mojzych M., Rykowski A., Heterocycles, 2004, 63, 1829-1838) disclose 7-methyl-5-phenyl-1H-pyrazolo[4,3-e]tetrazolo[4,5-b][1,2,4]triazine and synthesis of 3-methyl-5-methylsulfonyl-1-phenyl-1H-pyrazolo[4,3-e][1,2,4]triazine.

The object of the present invention was to provide novel compounds suitable for the treatment of neoplasms, especially the alimentary track cancers, in particular gastric cancer and/or colorectal cancer. The object of the present invention was also to provide new compounds having cytotoxic and cytostatic action. The object of the present invention was also to provide a method of synthesis such compounds, pharmaceutical compositions comprising such compounds and uses of such compounds.

These objects have been realized by means of the solutions presented in the attached claims of the patent. It has been unexpectedly found that that these objects may be realized using novel sulfonamide derivatives of 5-phenyl-7-methyl-pyrazole[4,3-e]tetrazole[4,5-b][1,2,4]triazine comprising L-proline methyl ester or 4-hydroxy-L-proline methyl ester.

The subject matter of the invention relates to a sulfonamide derivative of 7-methyl-5-phenyl-pyrazolo[4,3-e]tetrazolo[4,5-b][1,2,4]triazine of a general Formula 1:

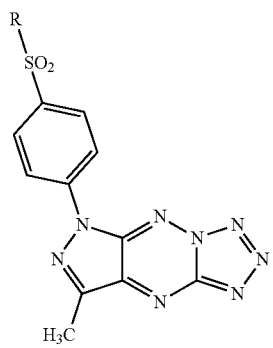

(Formula 1)

wherein R is proline methyl ester or 4-hydroxy-L-proline methyl ester.

Preferably, the compound according to the invention is a sulfonamide derivative of 7-methyl-5-phenyl-pyrazolo[4,3-e]tetrazolo[4,5-b][1,2,4]triazine comprising L-proline methyl ester in the sulfonamide group of Formula 2:

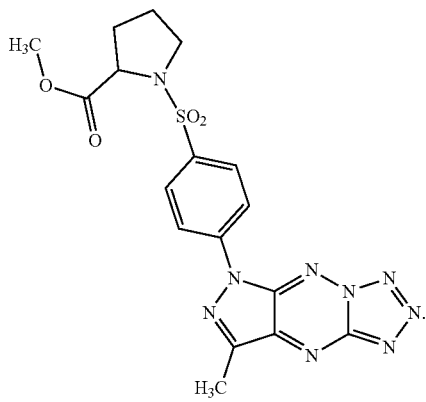

(Formula 2)

Preferably, the compound according to the invention is a sulfonamide derivative of 7-methyl-5-phenyl-pyrazolo[4,3-e]tetrazolo[4,5-b][1,2,4]triazine comprising 4-hydroxy-L-proline methyl ester in the sulfonamide group of Formula 3:

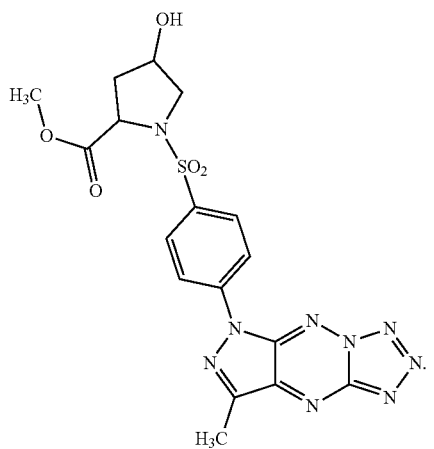

(Formula 3)

The subject matter of the invention further relates to a method of manufacturing a sulfonamide derivative of 7-methyl-5-phenyl-pyrazolo[4,3-e]tetrazolo[4,5-b][1,2,4]triazine of a general Formula 1, wherein R is proline methyl ester or 4-hydroxy-L-proline methyl ester, characterized in that 1-(para-chlorosulfonylphenyl)-3-methyl-5-methylsulfonyl-1H-pyrazolo[4,3e] [1,2,4]triazine is subjected to reaction with L-proline methyl ester hydrochloride or 4-hydroxy-L-proline methyl ester hydrochloride in anhydrous acetonitrile in the presence of sodium carbonate thus obtaining a suitable sulfonamide derivative with methylsulfone group at position 5 of 1H-pyrazolo[4,3-e][1,2,4]triazine system, which derivative is subsequently subjected to reaction with sodium azide in anhydrous ethanol.

Preferably, such obtained sulfonamide derivative of 7-methyl-5-phenyl-pyrazolo[4,3-e]tetrazolo[4,5-b][1,2,4]triazine of Formula 2 or 3, respectively, is purified by means of chromatography, more preferably with the use of liquid chromatography.

The subject matter of the invention further relates to a derivative as defined above for use as a medicament.

The subject matter of the invention further relates to a derivative as defined above for use as a medicament for the treatment of a neoplasm.

The subject matter of the invention further relates to a derivative as defined above for use as a medicament for the treatment of the alimentary track cancer.

Preferably, in the uses according to the invention the alimentary track cancer is gastric cancer.

Preferably, in the uses according to the invention the alimentary track cancer is colorectal cancer.

The subject matter of the invention further relates to a derivative as defined above for use as a cytostatic agent.

The subject matter of the invention further relates to a derivative as defined above for use as a cytotoxic agent.

The subject matter of the invention also relates to a pharmaceutical composition characterized in that it comprises the compound as defined above as an active compound, and a pharmaceutically acceptable carrier, diluent or excipient.

Preferably, the composition according to the invention comprises, as an active component, a derivative of a general Formula 1 according to the invention, wherein R is 4-hydroxy-L-proline methyl ester.

Sulfonamide derivatives of 7-methyl-5-phenyl-pyrazolo[4,3-e]tetrazolo[4,5-b][1,2,4]triazine of a general Formula 1, which are the subject matter of the present patent application, despite the presence of the known backbone of the pyrazolo[4,3-e]tetrazolo[4,5-b][1,2,4]triazine system, have a totally different structure than the compounds described in literature and are characterized by the presence of the sulfonamide group comprising L-proline methyl ester or 4-hydroxy-L-proline methyl ester, which gives those compounds their characteristic properties.

The sulfonamide derivative of 7-methyl-5-phenyl-pyrazolo[4,3-e]tetrazolo[4,5-b][1,2,4]triazine according to the invention, wherein R in the general Formula 1 is L-proline methyl ester, has the following structural formula:

Formula 2

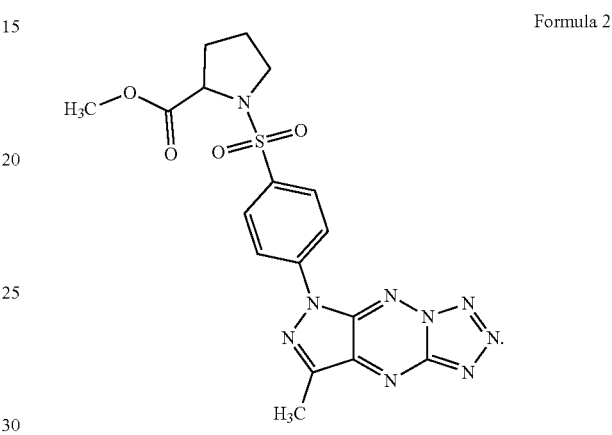

The sulfonamide derivative of 7-methyl-5-phenyl-pyrazolo[4,3-e]tetrazolo[4,5-b][1,2,4]triazine that is the subject matter of the present invention, wherein R in the general Formula 1 is 4-hydroxy-L-proline methyl ester, has the following structural formula:

Formula 3

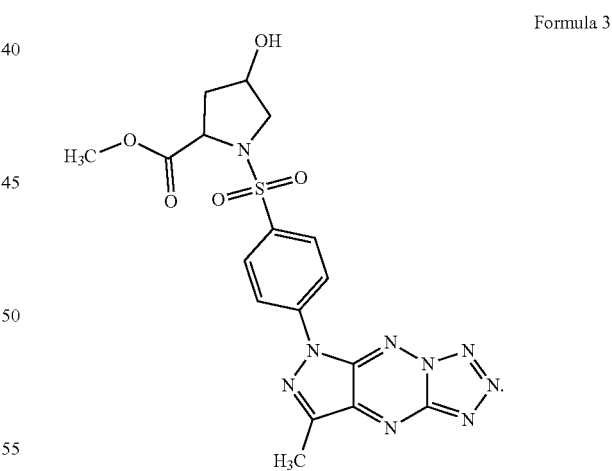

The tests and studies that have been carried out, both in vitro and in vivo, have shown that the compounds according to the invention exhibit anticancer, cytostatic, cytotoxic, antiapoptotic and antiproliferative action due to which they can be used as medicaments, in particular medicaments for the treatment of neoplasms, especially for the treatment of alimentary track cancers, in particular gastric cancer and/or colorectal cancer. Due to their properties, the compounds according to the invention may also be used as antiapoptotic, antiproliferative cytostatic and/or cytotoxic agents.

Anticancer activity of the novel sulfonamide derivatives of 7-methyl-5-phenyl-pyrazolo[4,3-e]tetrazolo[4,5-b][1,2,4]triazine comprising L-proline methyl ester or 4-hydroxy-L-proline methyl ester according to the invention in in vitro conditions was determined with the use of gastric cancer cells (AGS cell line) and colorectal cancer cells (DLD-1 cell line and HT-29 cell line). Cultures of such cancer cells were used to measure cytotoxicity of the compounds according to the invention and to assess their effect on DNA biosynthesis in the studied cancer cells. Additionally, the colorectal cancer cells lines (DLD-1 cell line and HT-29 cell line) were used to assess the effect of said compounds on selected biochemical markers of apoptosis, such as: loss of the asymmetric arrangement of phospholipids in cell membrane and a change in mitochondrial membrane potential. Cytotoxicity of the compounds according to the invention was measured by Carmichael's method and cell viability was determined using the tetrazolium salt (MTI) in MTT assay. The effect of the compounds on the process of DNA biosynthesis in the examined gastric cancer cells and colorectal cancer cells was assessed by measuring [$^3$H]-thymidine incorporation into DNA of the examined cells. Induction of apoptosis was examined by a method using fluorescein isothiocyanate-labelled Annexin V (Annexin V-FITC) which forms complexes with phosphatidylserine in the presence of calcium ions. The assessment of changes in mitochondrial potential was made using MitoScreen (JC-1) kit (BD Biosciences, USA).

The compounds according to the invention exhibit strong anticancer activity against the examined lines of neoplastic cells. A detailed description of determination of the anticancer activity of the compounds according to the invention was determined in in vitro conditions is presented in Example 2. Further, Table 1 presents the results of cytotoxic and cytostatic activity of the compounds according to the invention after 24 hours of incubation. Tables 2 and 3 and FIGS. 1 and 2 show the effect of the compounds according to the invention on the induction of apoptosis processes in the cancer cells: DLD-1 and HT-29. FIGS. 3 and 4 show the effect of the compounds according to the invention on mitochondrial membrane potential in the colorectal cancer cells (DLD-1 cell line and HT-29 cell line). Anticancer activity of an exemplary compound according to the invention (Formula 3) in in vivo conditions is presented in Example 3.

Sulfonamide derivatives of 7-methyl-5-phenyl-pyrazolo[4,3-e]tetrazolo[4,5-b][1,2,4]triazine comprising L-proline methyl ester or 4-hydroxy-L-proline methyl ester in the sulfonamide group according to the invention are obtained by a different synthesis method than the methods known in the prior art.

The method of manufacturing sulfonamide derivatives of 7-methyl-5-phenyl-pyrazolo[4,3-e]tetrazolo[4,5-b][1,2,4]triazine comprising L-proline methyl ester or 4-hydroxy-L-proline methyl ester in the sulfonamide group according to the invention is characterized in that 1-(para-chlorosulfonylphenyl)-3-methyl-5-methylsulfonyl-1H-pirazolo[4,3 e][1,2,4] triazine is subjected to reaction with L-proline methyl ester hydrochloride or 4-hydroxy-L-proline methyl ester hydrochloride, depending on the desired final product, in anhydrous acetonitrile in the presence of sodium carbonate and thus a suitable novel sulfonamide derivative with methylsulfone group in position 5 of 1H-pyrazolo[4,3-e][1,2,4]triazine system is obtained, which derivative is subsequently subjected to reaction with sodium azide in anhydrous ethanol and resultantly a suitable final sulfonamide derivative comprising, in the sulfonamide group, L-proline methyl ester (the compound of Formula 2) or 4-hydroxy-L-proline methyl ester (the compound of Formula 3), respectively, is obtained and subsequently said derivative is preferably purified by means of chromatography, preferably using liquid chromatography.

An exemplary method of manufacturing the novel sulfonamide derivatives of 7-methyl-5-phenyl-pyrazolo[4,3-e]tetrazolo[4,5-b][1,2,4]triazine comprising L-proline methyl ester or 4-hydroxy-L-proline methyl ester in the sulfonamide group according to the present invention is presented in Example 1 wherein spectroscopic data and melting temperatures of the obtained compounds according to the invention are given.

The compounds according to the invention may be used as such in the uses according to the invention or in the form of pharmaceutical compositions. A pharmaceutical composition according to the invention comprises, besides from the compound according to the invention as an active agent, a pharmaceutically acceptable carrier, diluent or excipient. Pharmaceutically acceptable carriers, diluents and excipients are known to persons skilled in the art of the present invention and they comprise liquid or non-liquid base of a composition. The term "acceptable" means herein that the components of the pharmaceutical composition used herein may be mixed with a pharmaceutically active component as defined herein, that is one and/or more compound according to the invention, and with another component in such a manner that there will be no interaction that could significantly reduce the pharmaceutical effectiveness of the composition in normal conditions of use. Pharmaceutically acceptable carriers, diluents or excipients used must have sufficiently high purity and sufficiently low toxicity to be suitable for administration in a subject to be treated, as is known in the field of the present invention. The pharmaceutical composition according to the present invention may be manufactured in a standard manner. Methods for manufacturing pharmaceutical compositions comprising at least one active component and a pharmaceutically acceptable carrier, diluent or excipient are known in the field of the present invention. The pharmaceutical compositions according to the invention which comprise, as an active component, at least one compound according to the invention may be used for the treatment of neoplasms, especially of the alimentary track cancers, in particular gastric cancer and/or colorectal cancer.

The present invention will be illustrated below by means of examples and figures which, however, are not supposed to limit in any manner the scope of the protection of the invention as defined in the claims. Unless indicated otherwise, known and/or commercially available devices, methods, reaction conditions, reagents and kit which are commonly used in the field of the present invention and which are recommended by the manufacturers of suitable reagents and kits were used.

EXAMPLE 1

Figure 1:
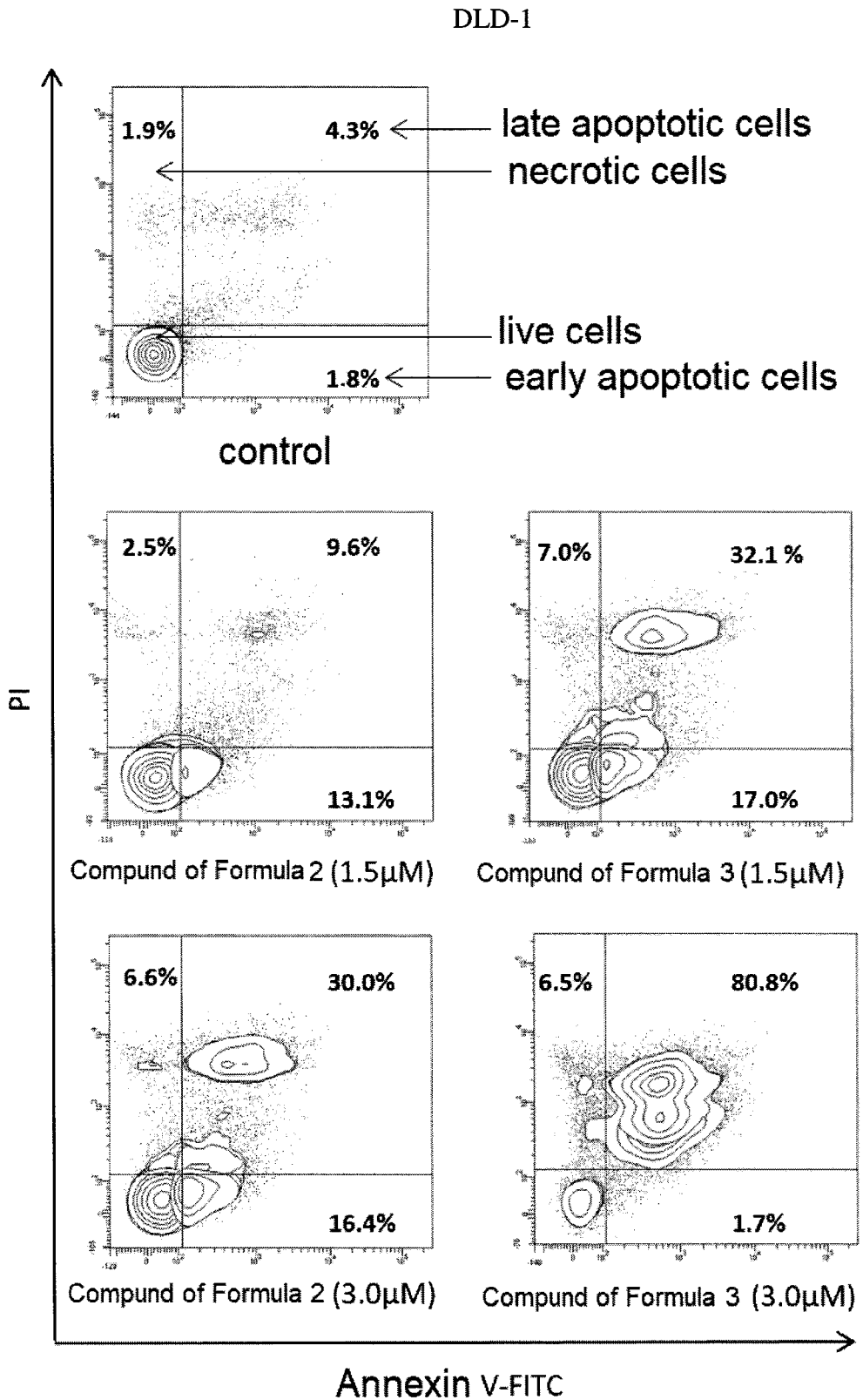
FIG. 1 shows the results of the study of apoptosis induction in DLD-1 colorectal cancer cells incubated for 24 hours with sulfonamide derivatives of 7-methyl-5-phenyl-pyrazolo[4,3-e]tetrazolo[4,5-b][1,2,4]triazine according to the invention at a concentration of 1.5 μM and 3.0 μM. The study was carried out with use of Annexin V and propidium iodide (PI).

A Method of Manufacturing 1-[4-(chlorosulfonyl)phenyl]-3-methyl-5-methylsulfonyl-1H-pyrazolo[4,3-e][1,2,4]triazine 1-phenyl-3-methyl-5-methylsulfonyl-1H-pyrazolo[4,3-e][1,2,4]triazine (1156 mg, 4 mmoles) was added to a flask containing 2 ml of chlorosulfonic acid cooled to 0-5° C. in a mixture of water and ice. Initially, the reaction was conducted at 0-5° C. for half an hour and subsequently in room temperature for 2 hours and the course of reaction was monitored on TLC plates. After the completion of reaction, the reaction mixture was poured on water with ice and was extracted using methylene chloride (4×50 ml). The combined extracts were dried over anhydrous $MgSO_4$. After evaporating methylene chloride in an evaporator, the raw product was purified in a chromatography column using a mixture of methylene chloride:methanol (50:1) as eluent. The product obtained was in the form of yellow s.

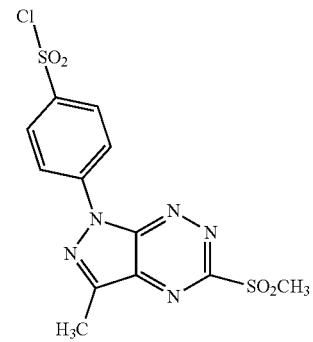

Yield 65%;
$^1$H NMR ($CDCl_3$) δ: 2.91 (s, 3H), 3.63 (s,3H), 8.29 (d, 2H, J = 9.2 Hz), 8.81 (d, 2H J = 9.2 Hz)

A Method of Manufacturing Methyl 1-(4-(3-methyl-5-methylsulfonyl-1H-pyrazolo[4,3-e][1,2,4]triazyn-1-yl)phenylsulfonyl)pyrrolidine-2 carboxylate and Methyl 4-hydroxy-1-(4-(3-methyl-5-methylsulfonyl-1H-pyrazolo[4,3-e][1,2,4]triazyn-1yl)phenylsulfonyl) pyrrolidine-2-carboxylate 1-(para-chlorosulfonylphenyl)-3-methyl-5-methylsulfonyl-1H-pyrazolo[4,3-e][1,2,4]triazine (0.5 mmol) obtained in the above manner was dissolved in anhydrous acetonitrile (5 ml) and added to 1.75 mmol of respective L-proline methyl ester or 4-hydroxy-L-proline methyl ester and 1.75 mmol of sodium carbonate. The reaction was conducted in room temperature until the substrate disappeared completely (TLC monitoring). After the completion of reaction the solvent was evaporated in an evaporator and the raw product was purified in a chromatography column using a mixture of $CH_2Cl_2$:MeOH (25:1) as eluent.

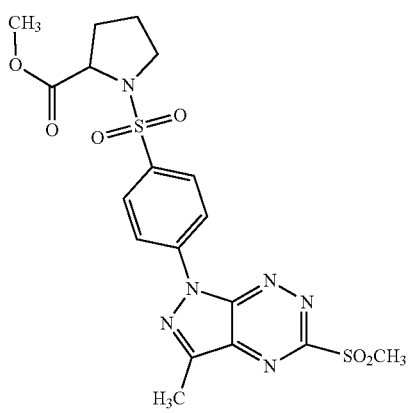

Yield 96%. Melting temperature: 79-83° C.;
$^1$H NMR (CDCl$_3$) δ: 1.81-1.90 (m, 1H), 1.96-2.07 (m, 2H), 2.09-2.17 (m, 1H), 2.88 (s, 3H), 3.39-3.45 (m, 1H), 3.48-3.53 (m, 1H), 3.60 (s, 3H), 3.73 (s, 3H), 4.40 (dd, 1H, J$_1$ = 8.7 Hz, J$_2$ = 3,3 Hz), 8.09 (d, 2H, J = 8.7 Hz), 8.63 (d, 2H, J = 8.7 Hz);
$^{13}$C NMR (CDCl$_3$) δ: 11.44, 24.68, 30.93, 40.76, 48.35, 52.46, 60.43, 119.96, 129.17, 137.12, 140.92 146.50, 148.08, 161.93, 172.36.

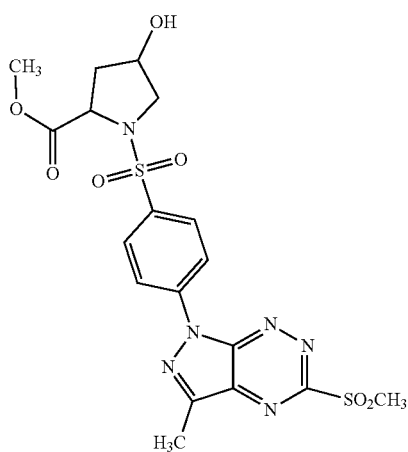

Yield 96%. Melting temperature: 112-114° C.;
$^1$H NMR (acetone) δ: 2.07-2.13 (m, 1H), 2.15-2.21 (m, 1H), 2.85 (s, 3H), 3.45 (dt, 1H, J$_1$ = 11.2 Hz, J$_2$ = 1.7 Hz), 3.59 (s, 3H), 3.65 (dd, 1H, J$_1$ = 10.8 Hz, J$_2$ = 4.2 Hz), 3.73 (s, 3H), 4.36 (t, 1H, J = 7.9 Hz), 4.42 (bs, 1H), 8.16 (d, 2H, J = 8.7 Hz), 8.67 (d 2H, J = 9.1 Hz);
$^{13}$C NMR (acetone) δ: 11.26, 23.33, 40.21, 41.15, 57.60, 60.83, 70.11, 120.80, 130.32, 137.24, 142.19, 147.31, 149.60, 162.92, 173.10.

A Method of Manufacturing Sulfonamide Derivatives of Formula 2 and 3

Sulfonamide derivatives with a methyl sulfone group (0.33 mmole) obtained in the above manner were dissolved in anhydrous ethanol (5 ml) and sodium azide (21 mg, 0.33 mmole) was added. The reaction mixture was refluxed until the substrate disappeared (TLC monitoring) and then, after evaporating the solvent, the raw product was purified using a chromatography column using CH2Cl2:MeOH system (50:1) as eluent.

Methyl 1-[4-(7-methyl-5H-pyrazol[4,3-e]tetrazolo[4,5-b][1,2,4]triazyn-5-yl) phenylsulfonyl]pyrrolidine-2-carboxylate (Compound of Formula 2)

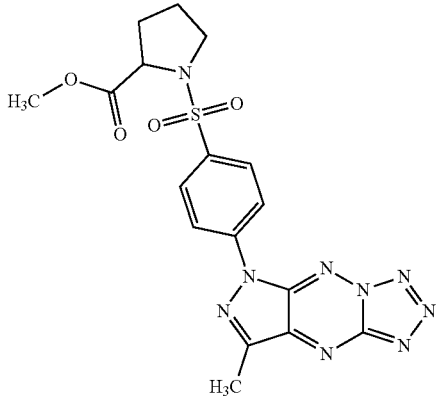

Yield 93%, Melting temperature: 125-127° C.;
$^1$H NMR (CDCl$_3$) δ: 1.82-188 (m, 1H), 1.95-2.05 (m, 2H), 2.10-2.15 (m, 1H), 2.88 (s, 3H), 3.38-3.45 (m, 1H), 3.48-3.54 (m, 1H) 3.60 (s, 3H), 4.39-4.42 (dd, 1H, J$_1$ = 8.8 Hz, J$_2$ = 4.0 Hz), 8.09 (d, 2H, J = 8.8 Hz), 8.63 (d, 2H, J - 8.8 Hz);
$^{13}$C NMR (CDCl$_3$) δ: 11.43, 24.68, 30.92, 40.76, 48.34, 52.46, 119.95, 129.17, 137.11, 140.92, 146.50, 148.02, 161.92, 172.35.

Methyl 4-hydroxy-1-[4-(7-methyl-5H-pyrazolo[4,3-e]tetrazolo[4,5-b][1,2,4]triazyn-5-yl)phenylsulfonyl] pyrrolidine-2-carboxylate (Compound of Formula 3)

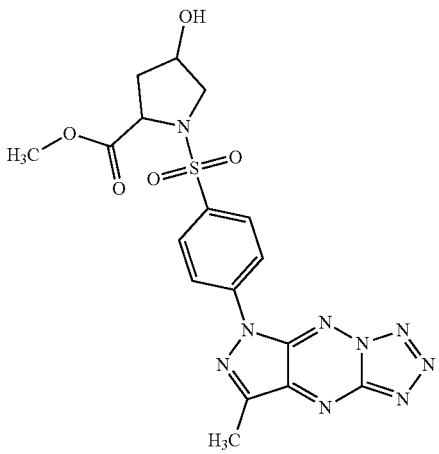

Yield 83%. Melting temperature: 122-128° C.;
$^1$H NMR (acetone) δ: 2.04-2.18 (m, 2H), 3.39 (d, 1H, J = 11.2 Hz), 2.85 (s, 3H), 3.62 (d, 1H, J = 12 Hz), 3.77 (s, 3H), 4.33 (d, 2H, J = 8.3 Hz), 4.57 (bs, 1H, OH), 8.08 (d, 2H, J = 9.2 Hz), 8.48 (d, 2H, J = 9.2 Hz);
$^{13}$C NMR (acetone) δ: 11.26, 41.14, 52.53, 57.59, 60.82, 70.22, 120.79, 130.32, 137.23, 142.19, 147.30, 149.60, 162.92, 173.09.

EXAMPLE 2

Anticancer, cytostatic, cytotoxic, antiapoptotic and antiproliferative activity of sulfonamide derivatives of 7-methyl-5-phenyl-pyrazolo[4,3-e]tetrazolo[4,5-b][1,2,4]triazine according to the invention was examined in in vitro and in vivo conditions in the following manner.

AGS human gastric cancer cells (ATCC CRL-1739, Manassas, VA, USA) were cultured in DMEM (Dulbecco's Modified Eagle's Medium) supplemented with 10% fetal bovine serum (FBS), 2 mM glutamine, 50 U/ml penicillin, 50 µg/ml streptomycin at 37° C., in atmosphere containing 5% $CO_2$. Subsequently, the cells were counted in a hemocytometer and transferred in the amount of $1 \times 10^6$ cells per well in 1 ml of culture medium from Costar flasks (Sigma, USA) to Nunc 6-well plates (Wiesbaden, Germany). The cells were transferred using calcium-free phosphate buffer with the addition of 0.05% trypsin and 0.02% EDTA. After 48 hours the culture medium was substituted with DMEM which did not contain phenol red and fetal bovine serum (FBS). Within the subsequent 24 hours the cells covered at least 80% of the surface of each plate well. The cells prepared in this manner were incubated with the examined compounds for 24 hours and then used for further experiments.

DLD-1 human colorectal cancer cells (ATCC CCL-221, Manassas, VA, USA) were grown in DMEM (Dulbecco's Modified Eagle's Medium) supplemented with 10% fetal bovine serum (FBS), 2 mM glutamine, 50 U/ml penicillin, 50 µg/ml streptomycin at 37° C., in atmosphere containing 5% of $CO_2$. Then the cells were counted in a hemocytometer and transferred in the amount of $1 \times 10^6$ cells per well in 1 ml of culture medium from Costar flasks (Sigma, USA) to Nunc 6-well plates (Wiesbaden, Germany). The cells were transferred using calcium-free phosphate buffer with the addition of 0.05% trypsin and 0.02% EDTA. After 48 hours the culture medium was substituted with DMEM which did not contain phenol red and fetal bovine serum (FBS). Within the subsequent 24 hours the cells covered at least 80% of the surface of each plate well. The cells prepared in this manner were incubated with the examined compounds for 24 hours and then used for further experiments.

HT-29 human colorectal cancer cells (ATCC HTB-38, Manassas, VA, USA) were cultured in McCoy's 5A medium supplemented with 10% fetal bovine serum (FBS), 2 mM glutamine, 50 U/ml penicillin, 50 µg/ml of streptomycin at 37° C., in atmosphere containing 5% $CO_2$. Subsequently, the cells were counted in a hemocytometer and were transferred in the amount of $1 \times 10^6$ cells per well in 1 ml of culture medium from Costar flasks (Sigma, USA) to Nunc 6-well plates (Wiesbaden, Germany). The cells were transferred using calcium-free phosphate buffer with the addition of 0.05% trypsin and 0.02% EDTA. After 48 hours the culture medium was substituted with McCoy's 5A medium which did not contain phenol red and fetal bovine serum (FBS). Within the subsequent 24 hours the cells covered at least 80% of the surface of each plate well. The cells prepared in this manner were incubated with the examined compounds for 24 hours and then used for further experiments.

Cytotoxicity of the examined compounds according to the invention was measured by Carmichael's method (Carmichael J et al, *Cancer Res.*, 1987, 47:943-946) and cell viability was determined using the tetrazolium salt (MT) in MTT assay. In living cells, the applied dye is converted to purple formazan under the influence of mitochondrial dehydrogenases. Such conversion does not take place in dead cells. The cells were incubated for 24 hours in an incubator that ensured suitable conditions, i.e.: at 37° C., in an atmosphere containing 5% $CO_2$ with medium containing different concentrations of the compounds according to the invention. After 24-hour incubation the cells were washed three times ($3 \times 1$ ml) in PBS. Subsequently, 1 ml PBS and 50 µl MTT in a concentration of 5 mg/cm$^3$ PBS were added and incubation was continued for 4 hours. After expiry of the required time, the substrate was removed and 1 ml 0.1M of hydrochloric acid in absolute isopropanol was added to the cells and the cells were left for 10 minutes. In a cell lysate prepared in such manner absorbance at 630 nm was measured. The result of absorbance obtained in the control cell cultures was assumed to be 100%. The viability of cells incubated in the presence of the examined compounds was expressed as percentage of the control values. The significance level p was determined by the nonparametric Mann-Whitney U test by means of SigmaStat software. The results at the significance level of $p<0.05$ were considered to be statistically significant. $IC_{50}$ values (inhibitory concentration 50—a concentration causing 50-percent reduction in cell survival) for AGS, DLD-1 and HT-29 cell lines were determined based on the analysis of relationship between the applied concentrations of the examined compounds according to the invention and cell survival level by means of Statistica 10 PL software.

The effect of the examined compounds according to the invention on the process of DNA biosynthesis was assessed by measuring incorporation of [$^3$H]-thymidine into DNA of the examined cells. The cells were incubated for 24 hours in an incubator that ensured suitable conditions, i.e.: at 37° C., in an atmosphere containing 5% $CO_2$ with medium containing different concentrations of the examined compounds according to the invention. The examined compounds were added to culture medium and were incubated for 24 hours. After that time the medium was replaced with fresh medium and 0.5 µCi [$^3$H]-thymidine (specific activity 6.7 Ci/mmol) was added to each well and the cells were further incubated for 4 hours in the incubator in an atmosphere containing 5% $CO_2$ at 37° C. After that time the medium was removed and the surface of cells was washed three times ($3 \times 1$ ml) with 0.05 mole Tris-HCl, having pH 7.4 and containing 0.11 mole NaCl. Subsequently, the cells were washed two times ($2 \times 1$ ml) with 5% trichloroacetic acid (TCA) solution and dissolved in 1 ml of 0.1 molar NaOH containing 1% SDS. After 5 minutes, the cell lysate obtained was transferred to scintillation vials containing 2 ml of scintillation fluid and radioactivity was measured. The intensity of DNA biosynthesis in the control cells, expressed in dpm of radioactive thymidine incorporated in DNA of the examined cells, per $1 \times 10^6$ cells, was assumed to be 100%. The values from the examined samples were expressed as percentage of the control value. The significance level p was determined by the nonparametric Mann-Whitney U test by means of SigmaStat software. The results at the significance level of p<0.05 were considered to be statistically significant. On the basis of obtained results $IC_{50}$ values (inhibitory concentration 50—a concentration inhibiting the incorporation of [$^3$H]-thymidine by 50%) were determined.

Table 1 below presents the results of the study of anticancer, cytostatic, cytotoxic and antiproliferative action of the compounds according to the invention against neoplastic cells.

FACSCanto H (BD Biosciences Systems, San Jose, CA, USA). The analysis of results was carried out by means of FACSDiva software (BD Biosciences Systems, San Jose, CA USA).

DLD-1 and HT-29 cells were incubated for 24 hours in an incubator at 37° C. in a 5% $CO_2$ atmosphere with medium containing the examined compounds according to the invention at specific concentrations. Both examined compounds were used at a concentration of 1.5 μM and 3.0 μM. After the incubation period, the medium was removed, a binding buffer included in the kit was added and the cells were suspended in the buffer. In order to calibrate the apparatus

TABLE 1

Cytostatic, cytotoxic and antiproliferative activity of the compounds according to the invention after 24-hour incubation.

| Compound | Cell survival $IC_{50}$ (μM) | | | [$^3$H]-thymidine $IC_{50}$ (μM) | | |
|---|---|---|---|---|---|---|
| | AGS | DLD-1 | HT-29 | AGS | DLD-1 | HT-29 |
| (Compound of Formula 2) | 0.92 ± 0.01 | 1.10 ± 0.01 | 1.73 ± 0.03 | 0.55 ± 0.01 | 0.56 ± 0.01 | 3.62 ± 0.02 |
| (Compound of Formula 3) | 0.80 ± 0.01 | 3.10 ± 0.02 | 3.13 ± 0.02 | 1.05 ± 0.01 | 1.55 ± 0.02 | 2.30 ± 0.02 |

Induction of apoptosis was examined by a method using fluorescein isothiocyanate-labelled Annexin V (Annexin V-FITC) which forms complexes with phosphatidylserine in the presence of calcium ions. The complexes were determined using FITC Annexin V Apoptosis Detection Kit II (BD Biosciences, USA) and a flow cytometer BD two control samples, i.e. a positive one and a negative one, were prepared. The positive control constituted a reference of control cells in which apoptosis was induced by the addition of 3% formaldehyde. Three control samples were prepared. The first sample contained control cells and propidium iodide, the second sample contained control cells and Annexin V-FITC and the third sample contained control cells, propidium iodide and Annexin V-FITC. After adding 2 µl of 3% formaldehyde the cells were placed in a refrigerator for 10 minutes. Cells that were not treated with any agent constituted the negative control. The cells from the control samples and the cells treated by the examined compounds according to the invention ($1\times10^6$ cells/ml) suspended in the buffer included in the kit were subjected to further examination. 200 µl suspension were taken from each examined sample and were transferred to test tubes. 3 µl Annexin V-FITC and 5 µl propidium iodide (PI) were added to each sample in room temperature and the samples were placed in a dark place for 15 minutes. Cell suspension prepared in this manner was analyzed within one hour in the flow cytometer BD FACSCanto II (BD Biosciences Systems, San Jose, CA, USA) by means of FACSDiva software. The results of the above experiment can be described as follows: live cells (double negative sample—lack of reaction with Annexin V and P), early apoptosis (Annexin V positive and PI negative sample), late apoptosis (Annexin V positive and PI positive sample) and necrosis (Annexin V negative and PI positive sample)

After 24-hour incubation of DLD-1 colorectal cancer cells with the compounds according to the invention the effect of said compounds on the induction of apoptosis was assessed. The compounds according to the invention were examined at a concentration of 1.5 µM and at a concentration of 3.0 µM. It was demonstrated that the action of both examined compounds results in programmed cell death (apoptosis). The population of control cells showed: 6.1% of apoptotic cells and 1.9% of necrotic cells. In the population of cells incubated with the compound of Formula 2 according to the invention, 22.7% of early and late apoptotic cells and 2.5% of necrotic cells were obtained at a concentration of 1.5 µM, whereas 46.4% of early and late apoptotic cells and 6.6% of necrotic cells were reported at a concentration of 3.0 µM. The population of cells incubated with the compound of Formula 3 according to the invention showed: 49.1% of apoptotic cells and 7.0% of necrotic cells at a concentration of 1.5 µM. The percentage of early and late apoptotic cells at 3.0 µM concentration of the compound of Formula 3 according to the inventions was 1.7% and 80.8%, respectively, whereas the percentage of necrotic cells was 6.5%.

The results of the study of apoptosis induction in DLD-1 colorectal cancer cells incubated for 24 hours with the compounds according to the invention at a concentration of 1.5 µM and 3.0 µM are presented in FIG. 1 together with representative cytograms from the analysis of DLD-1 cells and results in the form of mean values, which are presented in both FIG. 1 and Table 2 below.

After 24-hour incubation of HT-29 colorectal cancer cells with the compounds according to the invention the effect of said compounds on the induction of apoptosis was examined. It was observed that both compounds according to the invention, in both concentrations used, exhibit proapoptotic properties in HT-29 cell line. The population of control cells showed: 7.7% apoptotic cells and 2.3% necrotic cells. In the population of cells incubated with the compound of Formula 2 according to the invention the percentage of early and late apoptotic cells at a concentration of 1.5 µM was 9.0% and 4.7%, respectively, whereas the percentage of necrotic cells was 1.0%. In the population of cells incubated with the compound of Formula 2 according to the invention at a concentration of 3.0 µM, 19.0% of apoptotic cells and 2.7% necrotic cells were obtained. In the population of cells incubated with the compound of Formula 3 according to the invention, at a concentration of 1.5 µM, the percentage of early and late apoptotic cells was 30.5%, whereas the percentage of necrotic cells was 4.5%. In the population of cells incubated with the compound of Formula 3 according to the invention at a concentration of 3.0 µM, 25.2% early apoptotic cells, 13.7% late apoptotic cells and 2.6% necrotic cell were obtained.

Figure 2:
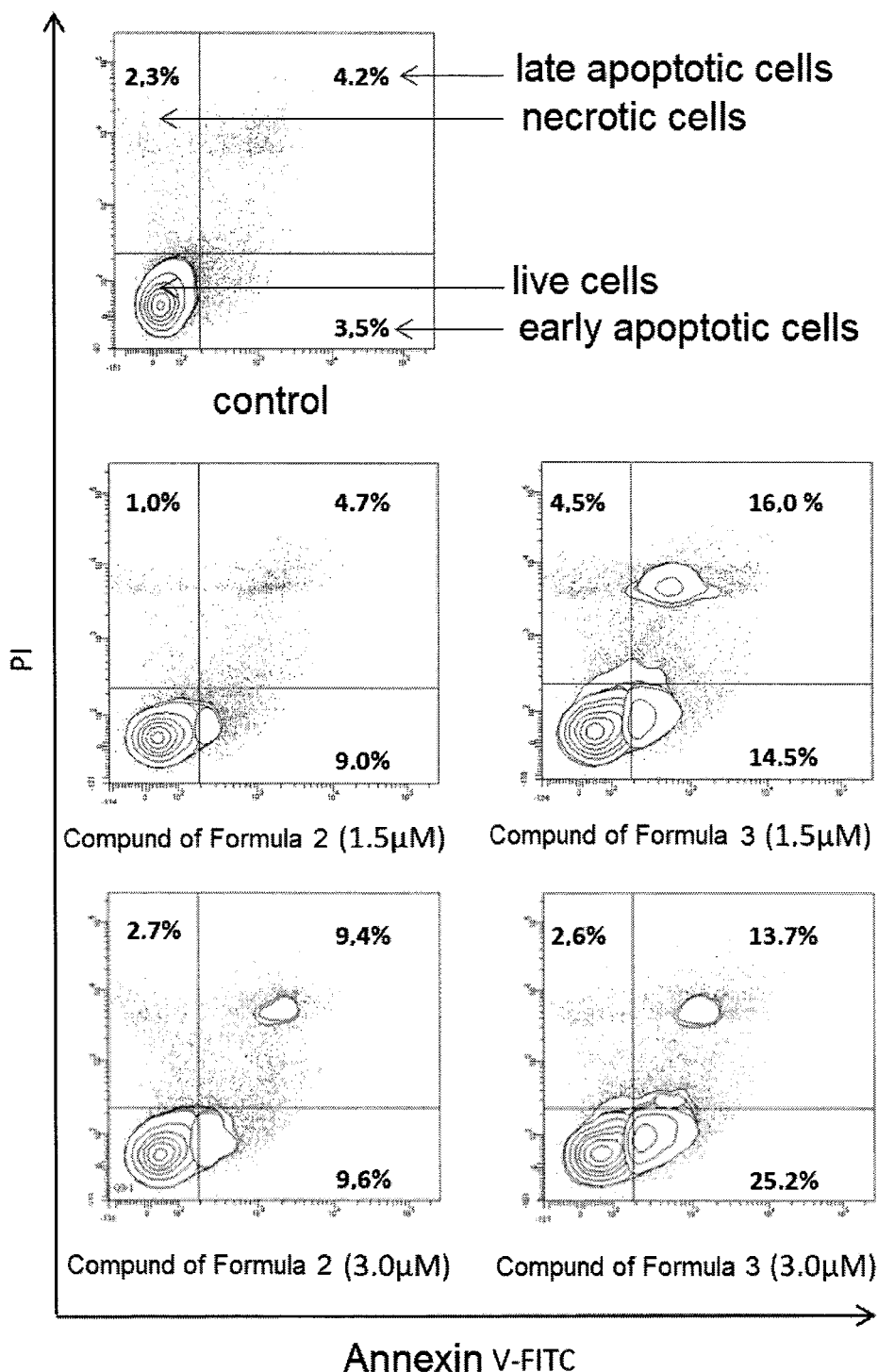
FIG. 2 shows the results of the study of apoptosis in HT-29 colorectal cancer cells incubated for 24 hours with sulfonamide derivatives of 7-methyl-5-phenyl-pyrazolo[4, 3-e]tetrazolo[4,5-b][1,2,4]triazine according to the invention at a concentration of 1.5 μM and 3.0 μM. The study was carried out with the use of Annexin V and propidium iodide (PI).

The results of the study of apoptosis induction in HT-29 colorectal cancer cells incubated for 24 hours with the compounds according to the invention at a concentration of 1.5 µM and 3.0 µM are presented in FIG. 2 together with representative cytograms from the analysis of HT-29 cells and with results in the form of mean values, which are presented in both FIG. 2 and Table 3 below.

TABLE 2

Induction of apoptosis in DLD-1 colorectal cancer cells incubated with the compounds according to the invention at a concentration of 1.5 µM and 3.0 µM for 24 hours. The study was carried out with the use of Annexin V and propidium iodide.

|  | Control | Compound of Formula 2 (1.5 µM) | Compound of Formula 2 (3.0 µM) | Compound of Formula 3 (1.5 µM) | Compound of Formula 3 (3.0 µM) |
| --- | --- | --- | --- | --- | --- |
| Live | 92.0% | 74.8% | 47.1% | 43.9% | 11.0% |
| Early apoptosis | 1.8% | 13.1% | 16.4% | 17.0% | 1.7% |
| Late apoptosis | 4.3% | 9.6% | 30.0% | 32.1% | 80.8% |
| Necrosis | 1.9% | 2.5% | 6.6% | 7.0% | 6.5% |

TABLE 3

Induction of apoptosis in HT-29 colorectal cancer cells incubated with the compounds according to the invention at a concentration of 1.5 µM and 3.0 µM for 24 hours. The examination was carried out with the use of Annexin V and propidium iodide.

|  | Control | Compound of Formula 2 (1.5 µM) | Compound of Formula 2 (3.0 µM) | Compound of Formula 3 (1.5 µM) | Compound of Formula (3.0 µM) |
|---|---|---|---|---|---|
| Live | 90.0% | 85.3% | 78.3% | 65.0% | 58.4% |
| Early apoptosis | 3.5% | 9.0% | 9.6% | 14.5% | 25.2% |
| Late apoptosis | 4.2% | 4.7% | 9.4% | 16.0% | 13.7% |
| Necrosis | 2.3% | 1.0% | 2.7% | 4.5% | 2.6% |

For the assessment of changes in mitochondrial potential JC-1 MitoScreen kit (BD Biosciences. USA) was used. DLD-1 and HT-29 cancer cells covering about 80% of the plate surface were incubated with the examined compounds according to the invention at specific concentrations in an incubator at 37° C. in 5% $CO_2$ atmosphere for 24 hours. Both examined compounds according to the invention were used at a concentration of 1.5 µM and 3.0 µM. After the incubation period, the medium was removed, the buffer included in the kit was added and the cells after washing two times were suspended in a mixture of JC-1 dye (5,5',6,6'-tetrachloro-1,1',3,3'-tetraethylbenzimidazol carbocyanine iodide) with a buffer at a concentration of 10 µg/ml. Subsequently, the samples were incubated in darkness for 15 minutes, washed with PBS solution and subjected to immediate analysis with the use of BD FacsCanto II flow cytometer; the results were assessed with the use of BD FacsDiva software. In live intact cells JC-1 dye accumulates in mitochondria and forms orange fluorescing aggregates. A decrease in mitochondrial potential $\Delta\Psi_m$ is characterized by disintegration of these aggregates and green fluorescence.

After 24-hour incubation of DLD-1 colorectal cancer cells with the compounds according to the invention the effect of said compounds on the mitochondrial membrane potential $\Delta\Psi$m was assessed. The obtained results of cytometric analysis of DLD-1 cells treated with the novel derivatives clearly show mitochondrial depolarization. In the case of control cells a decrease of $\Delta\Psi_m$ was observed in 0.2% of cell population.

Both compounds in the concentrations used decreased the mitochondrial membrane potential in DLD-1 colorectal cancer cells. The use of the compound of Formula 2 according to the invention at a concentration of 1.5 µM lead to a decrease of $\Delta\Psi_m$ in 48.9% of the cell population and at a concentration of 3.0 µM, a decrease occurred in 63.8% of the cell population, whereas the use of the compound of Formula 3 according to the invention at a concentration of 1.5 µM lead to a decrease of $\Delta\Psi_m$ in 49.5% of the cell population and at a concentration of 3.0 µM, a decrease occurred in 71.3% of the cell population.

Figure 3:
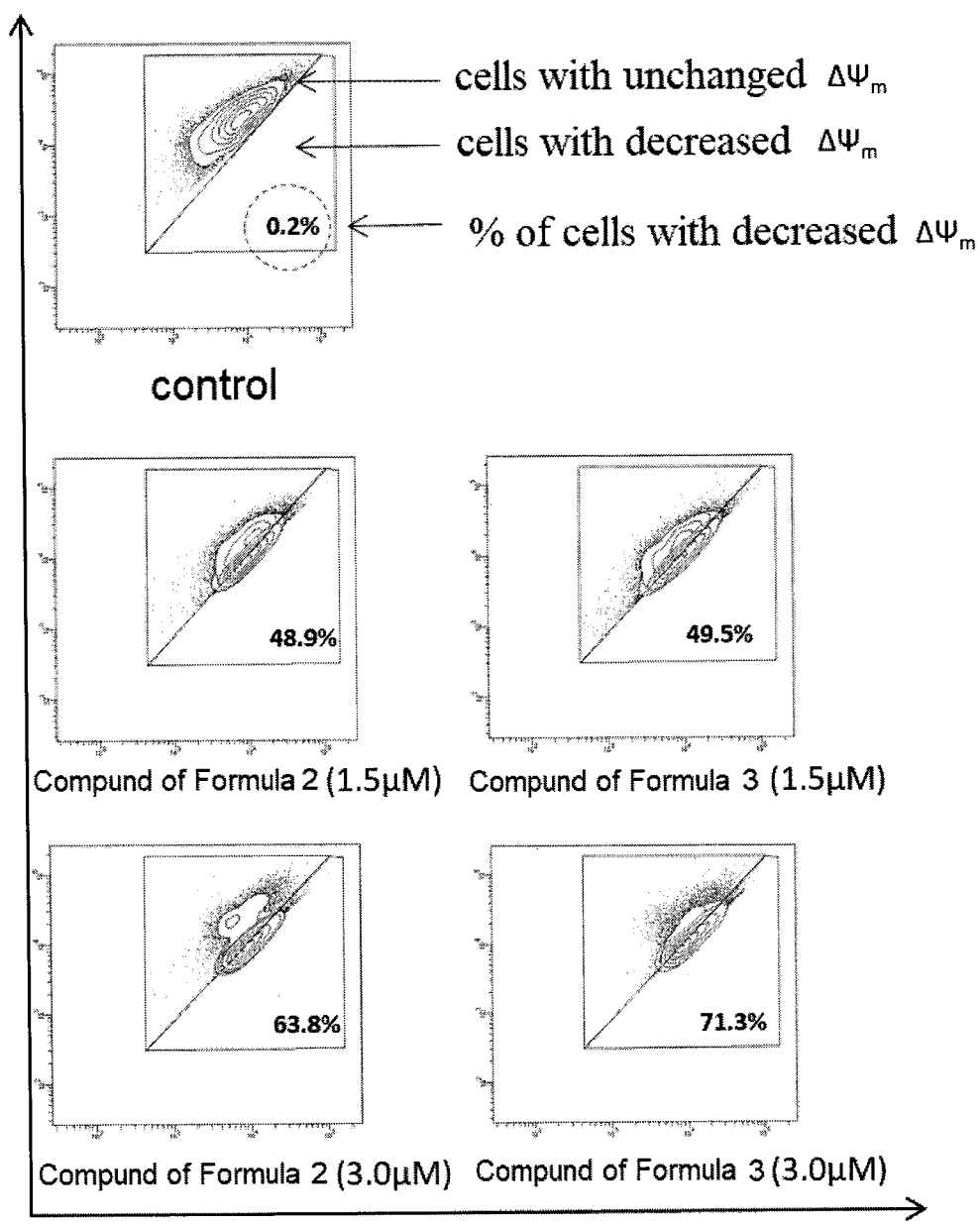
FIG. 3 shows the results of assessment of a decrease in mitochondrial membrane potential in DLD-1 colorectal cancer cells incubated for 24 hours with sulfonamide derivatives of 7-methyl-5-phenyl-pyrazolo[4,3-e]tetrazolo[4,5-b][1,2,4]triazine according to the invention at a concentration of 1.5 μM and 3.0 μM. The study was carried out with the use of JC-1 dye.

The results of the assessment of mitochondrial membrane potential decrease in DLD-1 colorectal cancer cells incubated for 24 hours with the compounds according to the invention at a concentration of 1.5 µM and 3.0 µM are presented in FIG. 3 together with representative cytograms from the analysis of the examined DLD-1 cells and results in the form of mean values.

After 24-hour incubation of HT-29 colorectal cancer cells with the compounds according to the invention the effect of these compounds on mitochondrial membrane potential was examined. The examined compounds were used at a concentration of 1.5 µM and 3.0 µM. It was observed that both examined compounds according to the invention decrease the mitochondrial membrane potential in HT-29 cells. In the population of control cells 4.8% of the population had a decreased $\Delta\Psi_m$. The use of the compound of Formula 2 according to the invention at a concentration of 1.5 µM lead to a decrease of $\Delta\Psi_m$ in 25.7% of the cell population and at a concentration of 3.0 µM a decrease occurred in 79.7% of the cell population, whereas the use of the compound of Formula 3 according to the invention at a concentration of 1.5 µM lead to a decrease of $\Delta\Psi_m$ in 26.9% of the cell population and at a concentration of 3.0 µM a decrease occurred in 81.0% of the cell population.

Figure 4:
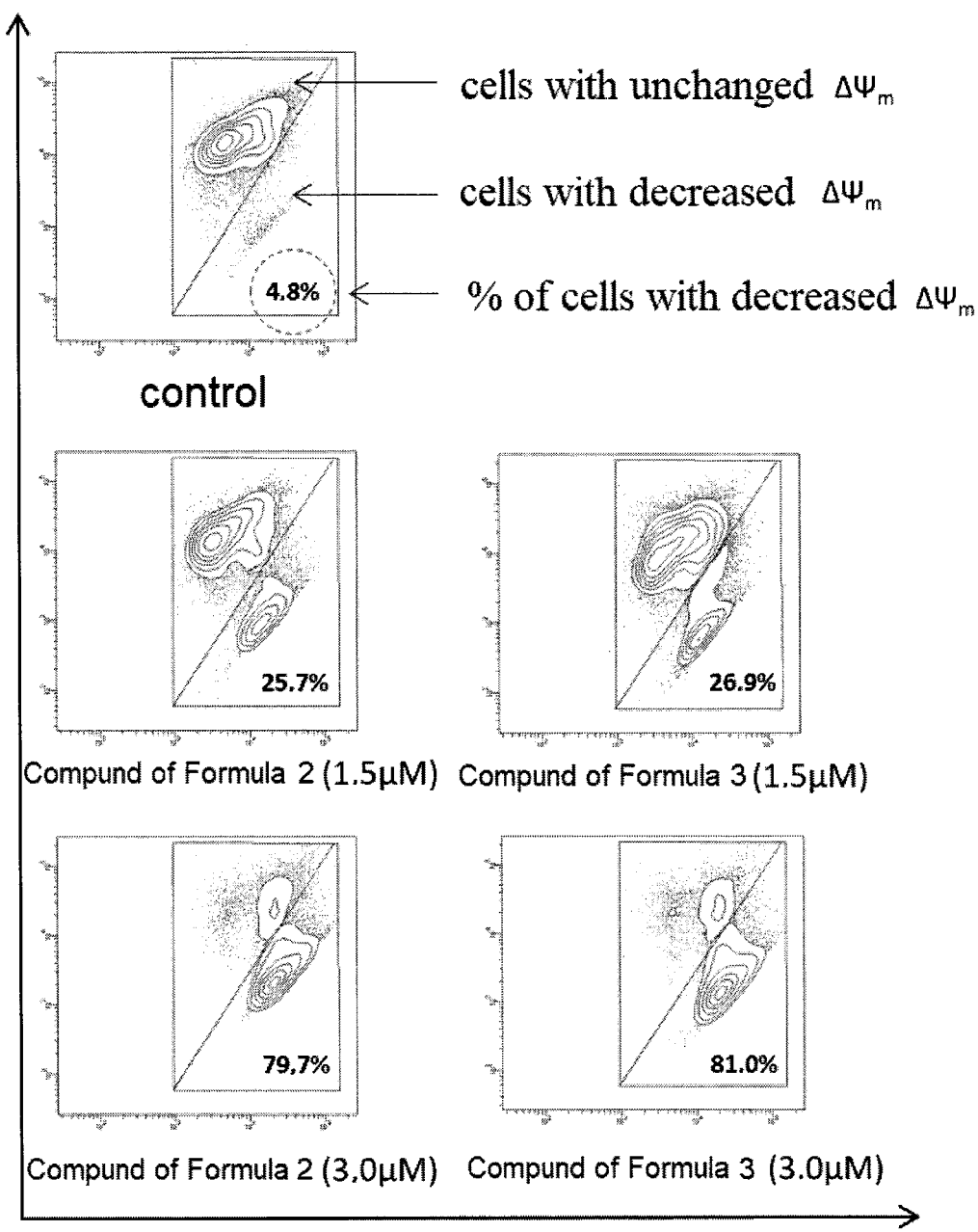
FIG. 4 shows the results of assessment of a decrease in mitochondrial membrane potential in HT-29 colorectal cancer cells incubated for 24 hours with sulfonamide derivatives of 7-methyl-5-phenyl-pyrazolo[4,3-e]tetrazolo[4,5-b][1,2,4]triazine according to the invention at a concentration of 1.5 μM and 3.0 μM. The study was carried out with the use of JC-1 dye.

The results of the assessment of mitochondrial membrane potential decrease in HT-29 colorectal cancer cells incubated for 24 hours with the compounds according to the invention at a concentration of 1.5 µM and 3.0 µM are presented in FIG. 4 together with representative cytograms from the analysis of the examined HT-29 cells and results in the form of mean values.

EXAMPLE 3

The second stage of the study was carried out with the use of animals (Cby.Cg-Foxn1nu/J mice, females) (Jackson Laboratory, USA). This strain exhibits a defect of thymic epithelium (athymic) and hair follicle defect (homozygous females) and is commonly used for the study of substances that modulate the neoplasmic growth. All procedures were carried out in accordance with the guidelines for experiments in animals and a protocol approved by the Local Ethics Committee (Resolution No. August 2018).

The studies in in vivo conditions were carried out in the Centre of Experimental Medicine of the Medical University of Bialystok. It is a modern institution which ensures a high standard of SPF barrier animal facilities. Animals are housed in a room with hypertension, in the optimal temperature of 22° C., 55% air humidity, with fifteen air changes per hour (with the speed not exceeding 0.3 m/s) and 12:12 light-dark cycle. The animals were under 24-hour monitoring and period controls of both the animals (in accordance with FELASA recommendations) and the rooms in which they were housed were carried out. The Centre for Experimental Medicine has a Good Laboratory Practice (GLP) certificate.

During the initial studies the mice were divided into two groups. The animals from the first group had a subcutaneous injection, on the dorsal side, of 50 µl of suspension containing a hundred million DLD-1 cells in PBS, whereas the mice from the second group had a subcutaneous injection of 50 µl of suspension containing a hundred million HT-29 cells in PBS in accordance with the methodology described by Shinohara et al. (Shinohara N. Tsuduki T. Ito J et al. *Biochim Biophys Acta*. 2012. 1821. 980-988).

After the first week, when tumours reached about 5 mm in diameter, i.e. the size which according to literature data is suitable for carrying out further steps of examination, the mice began receiving subcutaneous injections of the sulfonamide derivative of 7-methyl-5-phenyl-pyrazolo[4,3-e]tetrazolo[4,5-b][1,2,4]triazine comprising 4-hydroxy-L-proline methyl ester in the sulfonamide group according to the invention (the compound of Formula 3) in a dose of 50 µg/kg once a day for two weeks. The moment of administration of the compound was marked as time 0. The control group was constituted by animals that received subcutaneously 50 µl of 10% DMSO in PBS (the solvent for the compound of Formula 3). Before the administration of the sulfonamide derivative of 7-methyl-5-phenyl-pyrazolo[4,3-e]tetrazolo[4,5-b][1,2,4]triazine comprising 4-hydroxy-L-proline methyl ester in the sulfonamide group according to the invention (time 0), after the first week (time 1) and the second week (time 2) of administering this compound, the sizes of tumours were measured in two dimensions by means of a digital calliper. The volume of tumours was expressed in mm3 in accordance with the calculations that were described by Feldman et al. (Feldman J P. Goldwasser R. Mark S. Schwartz J. Orion I. *JAQM*. 2009.4.455-462).

Figure 5:
FIG. 5 shows the results of assessment of a decrease in mitochondrial membrane potential in HT-29 colorectal cancer cells incubated for 24 hours with sulfonamide derivatives of 7-methyl-5-phenyl-pyrazolo[4,3-e]tetrazolo[4,5-b][1,2,4]triazine according to the invention at a concentration of 1.5 μM and 3.0 μM. The study was carried out with the use of JC-1 dye.
Figure 6:
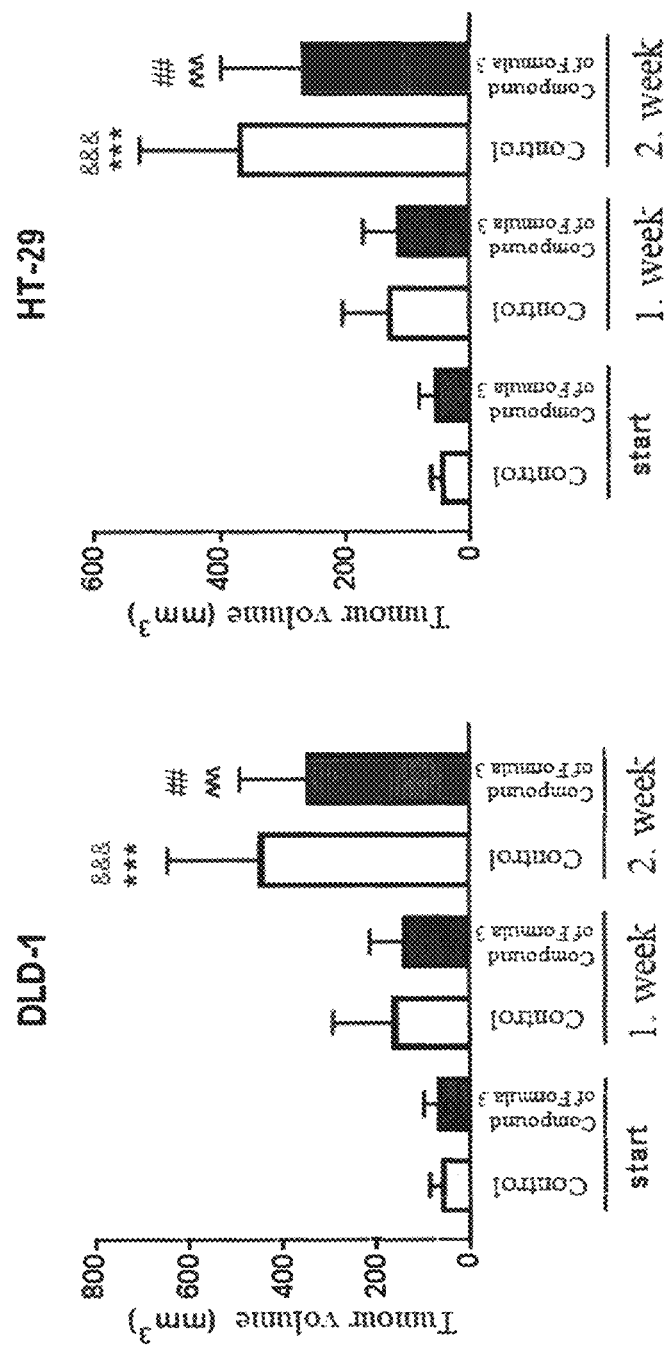
FIG. 6 shows the results of the study of the effect of the sulfonamide derivative of 7-methyl-5-phenyl-pyrazolo[4,3-e]tetrazolo[4,5-b][1,2,4]triazine comprising 4-hydroxy-L-proline methyl ester according to the invention (the compound of Formula 3) on the tumour volume in mice with DLD-1 and HT-29 xenografts.
Figure 7:
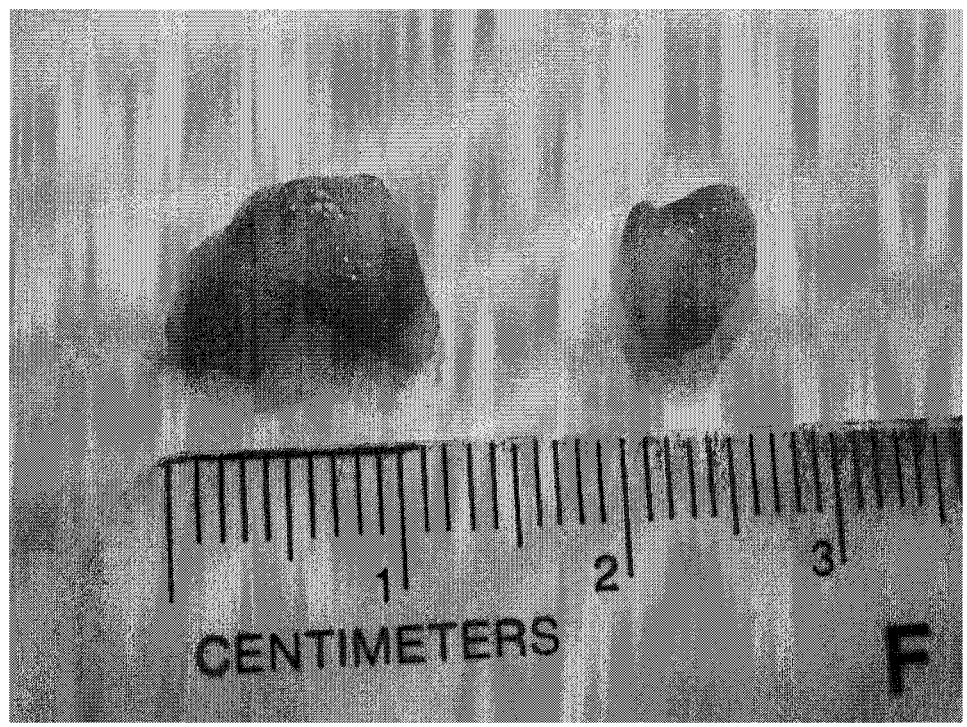
FIG. 7 shows the tumour size in a control group (on the left) and in a group that received the sulfonamide derivative of 7-methyl-5-phenyl-pyrazolo[4,3-e]tetrazolo[4,5-b][1,2,4]triazine comprising 4-hydroxy-L-proline methyl ester according to the invention (the compound of Formula 3) (on the right) in mice with DLD-1 xenografts after two weeks of the experiment.
Figure 8:
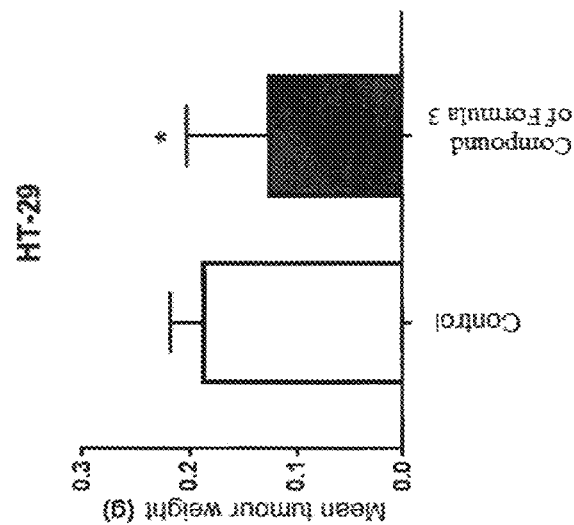
FIG. 8 shows mean tumour weights in the control group and in the group that received the sulfonamide derivative of 7-methyl-5-phenyl-pyrazolo[4,3-e]tetrazolo[4,5-b][1,2,4]triazine comprising 4-hydroxy-L-proline methyl ester according to the invention (the compound of Formula 3) in mice with DLD-1 and HT-29 xenografts after two weeks of the experiment (* vs. Control).
Figure 8:
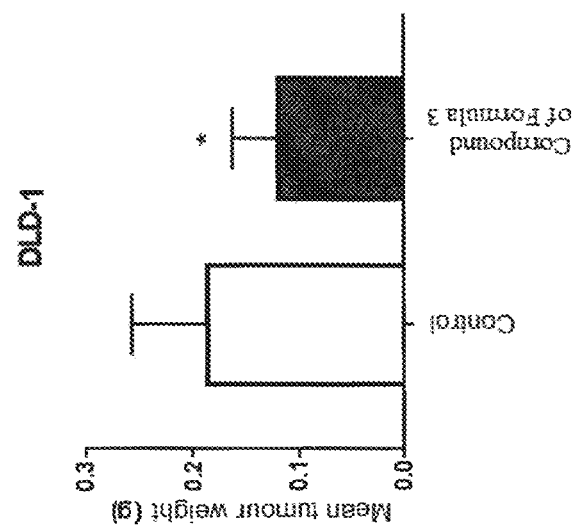

In the group of mice with DLD-1 and HT-29 xenografts statistically significant inhibition of tumour growth was observed in animals receiving the compound of Formula 3 according to the invention after the second week of the experiment in comparison with the control group (p<0.001) (FIGS. 5 and 6). Statistically significant reduction in tumour weight was also observed post mortem in the groups of mice with DLD-1 and HT-29 xenograft receiving the compound of Formula 3 in comparison with the control (p<0.05) (FIGS. 7 and 8).

Figure 9:
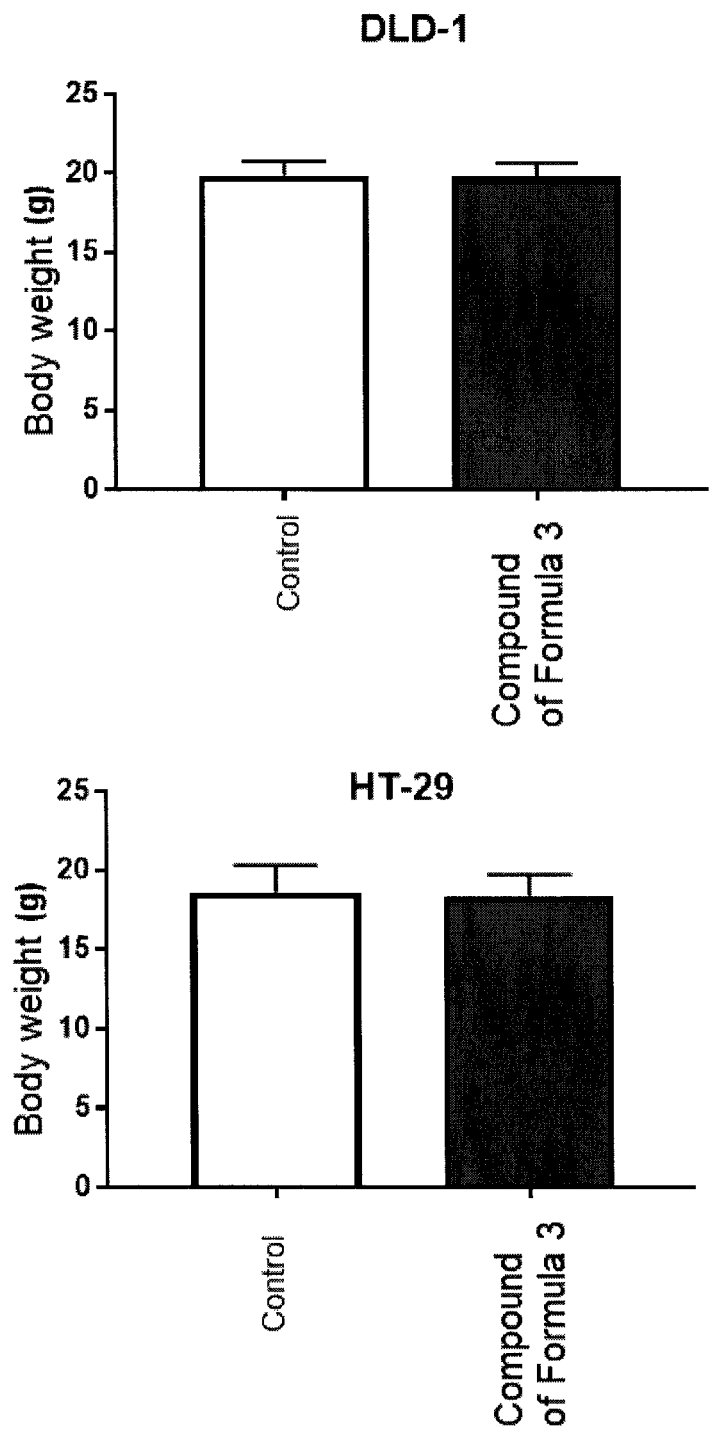
FIG. 9 shows the results of the study of the effect of the sulfonamide derivative of 7-methyl-5-phenyl-pyrazolo[4,3-e]tetrazolo[4,5-b][1,2,4]triazine comprising 4-hydroxy-L-proline methyl ester according to the invention (the compound of Formula 3) on the body weight of mice with DLD-1 and HT-29 xenografts after two weeks of the experiment.

Additionally, the effect of the compound of Formula 3 on the body weight of the animals after the two-week therapy was assessed. No significant differences were observed between the group that received the compound of Formula 3 according to the invention and the control (FIG. 9), which confirms the lack of a negative effect of the examined compound on animal welfare.

Figure 10:
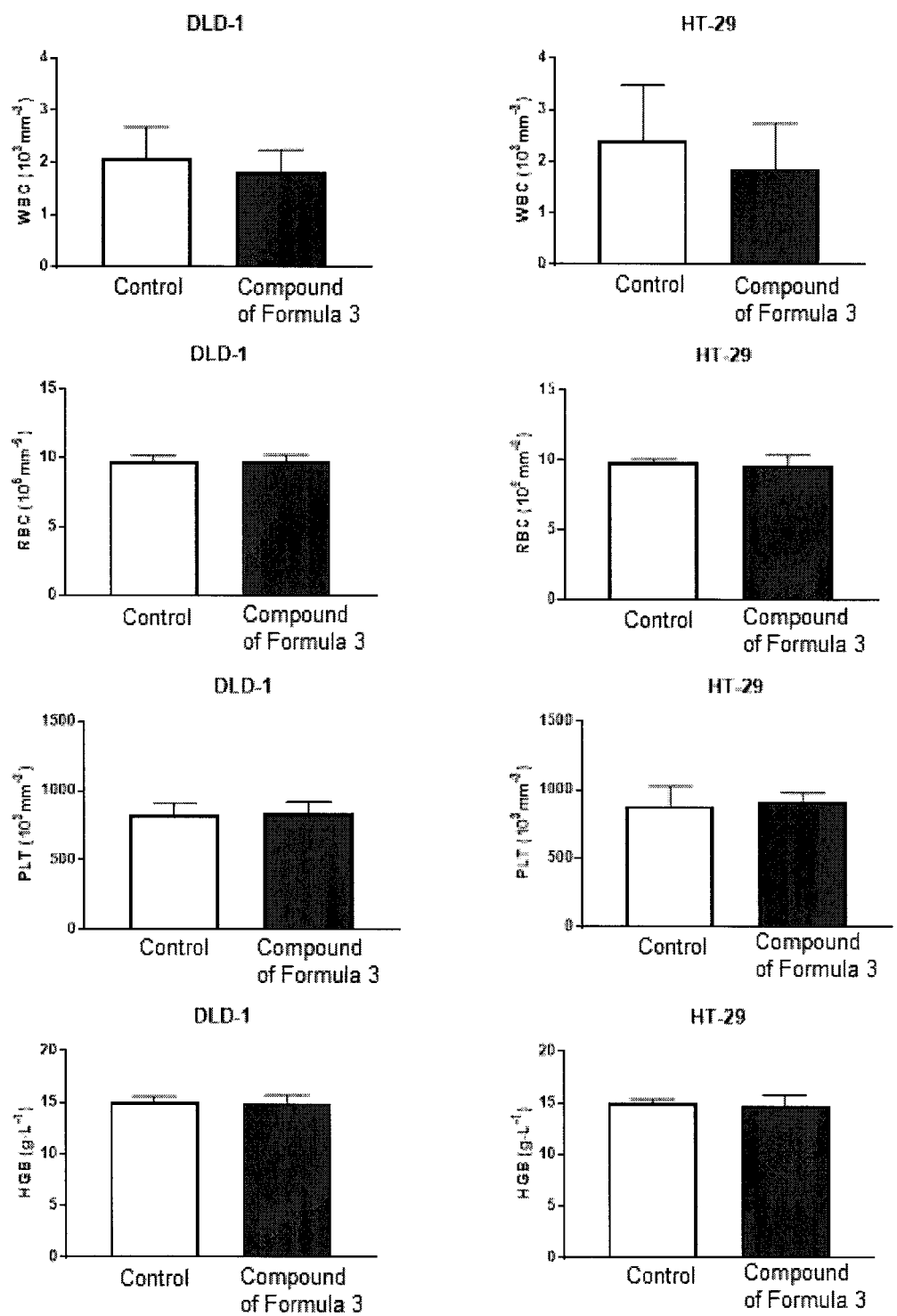
FIG. 10 shows the results of the study of the effect of the sulfonamide derivative of 7-methyl-5-phenyl-pyrazolo[4,3-e]tetrazolo[4,5-b][1,2,4]triazine comprising 4-hydroxy-L-proline methyl ester according to the invention (the compound of Formula 3) on the hematologic parameters in mice with DLD-1 and HT-29 xenografts after two weeks of the experiment.
Figure 11:
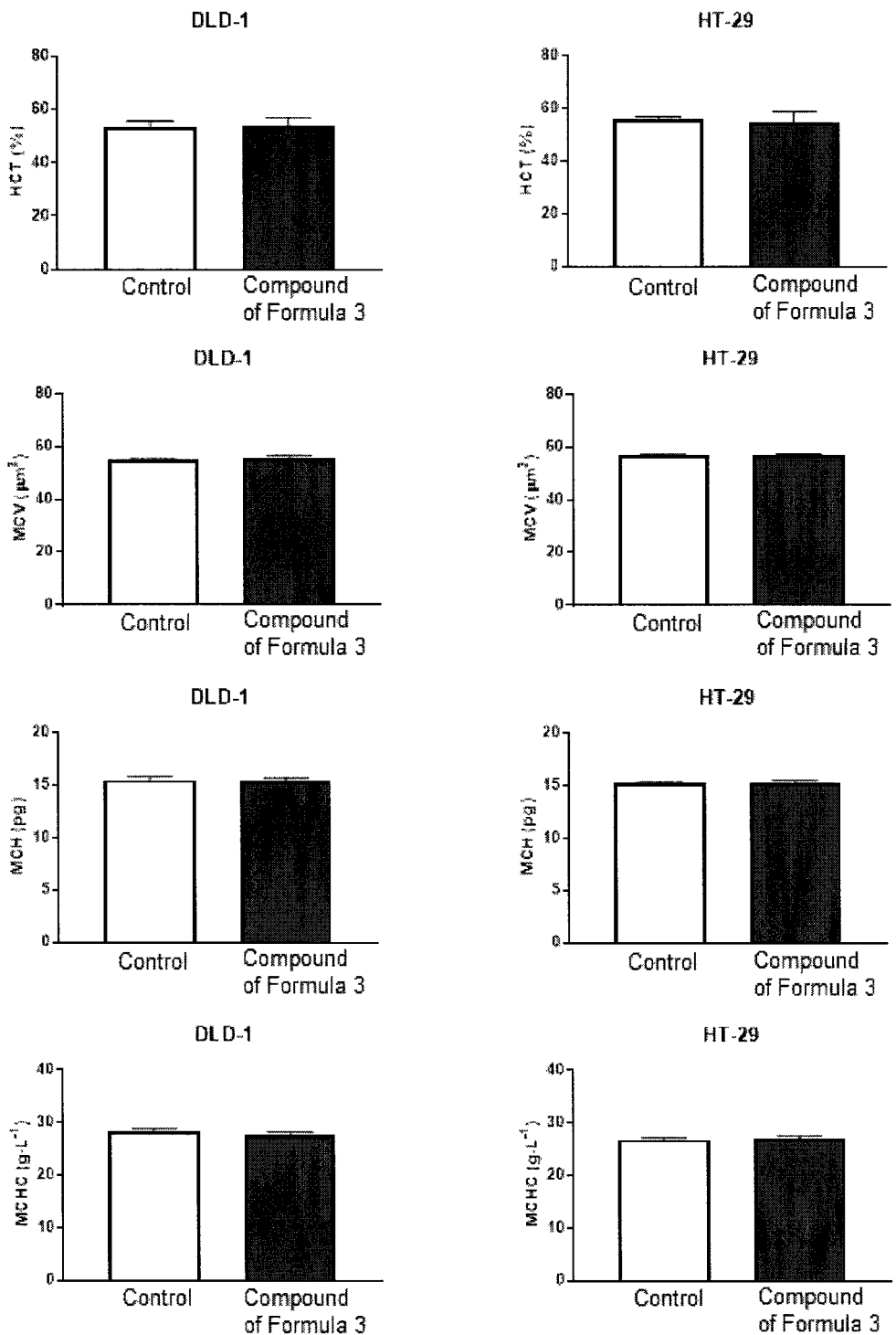
FIG. 11 shows the results of the study of the effect of the sulfonamide derivative of 7-methyl-5-phenyl-pyrazolo[4,3-e]tetrazolo[4,5-b][1,2,4]triazine comprising 4-hydroxy-L-proline methyl ester according to the invention (the compound of Formula 3) on the hematologic parameters in mice with DLD-1 and HT-29 xenografts after two weeks of the experiment.

Haematological analysis after the two-weak therapy did not reveal any statistically significant changes in such parameters as: white blood cells (WBC), red blood cells (RBC), platelets (PLT), haematocrit (HCT), haemoglobin (HGB), mean corpuscular volume (MCV), mean corpuscular haemoglobin (MCH), mean corpuscular haemoglobin concentration (MCHC) (FIG. 10, 11). This demonstrates relative safety of 7-methyl-5-phenyl-pyrazolo[4,3-e]tetrazolo[4,5-b][1,2,4]triazine comprising 4-hydroxy-L-proline methyl ester in the sulfonamide group according to the invention (the compound of Formula 3).

The studies conducted have shown that the compounds according to the invention exhibit strong anticancer, cytostatic, cytotoxic, antiapoptotic and antiproliferative effects. The studies conducted have also shown that the examined compounds according to the invention inhibit DNA biosynthesis in neoplastic cells, in particular, gastric cancer cells and colorectal cancer cells. The studies conducted have further shown that the compounds according to the invention exhibit high anticancer, cytostatic, cytotoxic, antiapoptotic and antiproliferative activity with respect to neoplastic cells, in particular gastric cancer cells and colorectal cancer cells, and thus they may be used in the treatment of neoplasms, in particular the alimentary track cancers, especially gastric cancer and colorectal cancer.

What is claimed is:

1. A sulfonamide derivative of 7-methyl-5-phenyl-pyrazolo [4,3-e] tetrazolo [4,5-b][1,2,4]triazine of Formula 1:

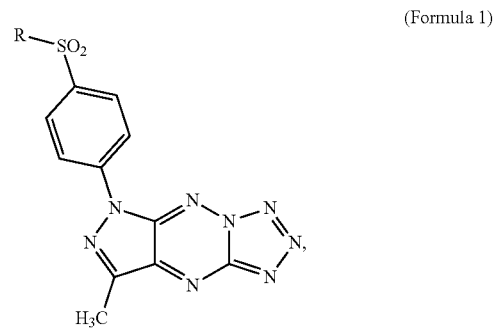

(Formula 1)

wherein R is L-proline methyl ester or 4-hydroxy-L-proline methyl ester.

2. The sulfonamide derivative according to claim 1, wherein R is L-proline methyl ester, and the sulfonamide derivative of 7-methyl-5-phenyl-pyrazolo[4,3-e] tetrazolo [4,5-b][1,2,4]triazine, is of Formula 2:

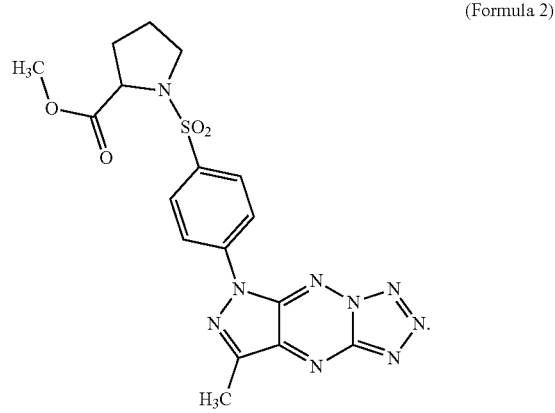 [SMILES: COC(=O)C1CCCN1S(=O)(=O)c1ccc(-n2nc(C)c3nc4nnnn4nc32)cc1]

(Formula 2)

3. The sulfonamide derivative according to claim 1, wherein R is 4-hydroxy-L-proline methyl ester, and the sulfonamide derivative of 7-methyl-5-phenyl-pyrazolo[4,3-e] tetrazolo [4,5-b][1,2,4]triazine is of Formula 3:

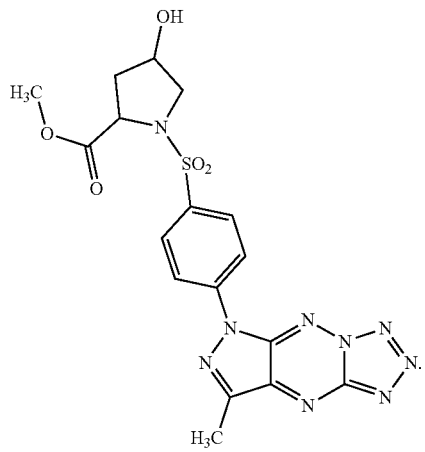

(Formula 3)

4. A method of manufacturing a sulfonamide derivative of 7-methyl-5-phenyl-pyrazolo[4,3-e] tetrazolo [4,5-b][1,2,4] triazine of Formula 1:

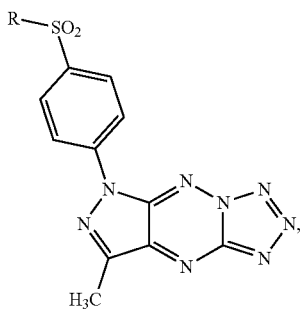

(Formula 1)

wherein R is L-proline methyl ester or 4-hydroxy-L-proline methyl ester, the method comprising:
reacting 1-(para-chlorosulphonylphenyl)-3-methyl-5-methylsulphonyl-1H-pyrazolo [4.3-e][1.2.4]triazine with L-proline methyl ester hydrochloride or 4-hydroxy-L-proline methyl ester hydrochloride in anhydrous acetonitrile in the presence of sodium carbonate thereby obtaining an intermediate that is a sulfonamide derivative with a methylsulfone group at position 5 of a 1H-pyrazolo[4,3-e][1,2,4]triazine system, and
reacting the intermediate with sodium azide in anhydrous ethanol thereby obtaining the sulfonamide derivative of 7-methyl-5-phenyl-pyrazolo[4,3-e] tetrazolo [4,5-b][1,2,4]triazine.

5. The method of manufacturing according to claim 4, wherein the sulfonamide derivative of 7-methyl-5-phenyl-pyrazolo [4,3-e]tetrazolo [4,5-b][1,2,4]triazine is of Formula 2

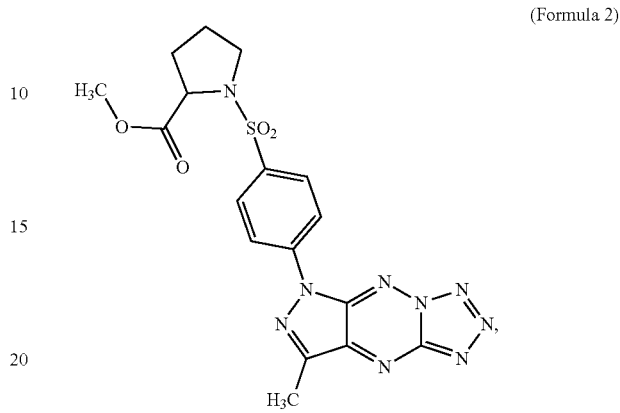

(Formula 2)

and
the method further comprises purifying the sulfonamide derivative of 7-methyl-5-phenyl-pyrazolo[4,3-e]tetrazolo [4,5-b][1,2,4]triazine by means of chromatography.

6. The method of manufacturing according to claim 5, wherein the chromatography is liquid chromatography.

7. The method of manufacturing according to claim 4, wherein the sulfonamide derivative of 7-methyl-5-phenyl-pyrazolo[4,3-e] tetrazolo [4,5-b][1,2,4]triazine is of Formula 3

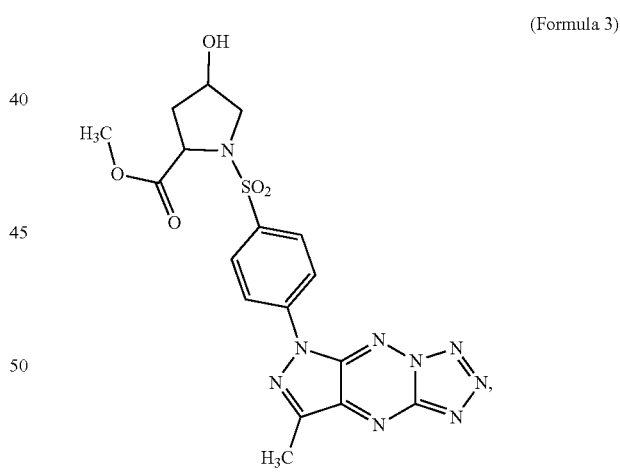

(Formula 3)

and
the method further comprises purifying the sulfonamide derivative of 7-methyl-5-phenyl-pyrazolo[4,3-e]tetrazolo [4,5-b][1,2,4]triazine by means of chromatography.

8. The method of manufacturing according to claim 7, wherein the chromatography is liquid chromatography.

9. A method of treating a cancer in a patient, said method comprising the step of administering a therapeutically effective amount of the sulfonamide derivative of claim 1 to the patient, wherein the sulfonamide derivative treats the cancer in the patient.

10. The method of claim 9, wherein the cancer is a neoplasm.

11. The method of claim 9, wherein the cancer is an alimentary track cancer.

12. The method of claim 11, wherein the alimentary track cancer is gastric cancer.

13. The method of claim 11, wherein the alimentary track cancer is colorectal cancer.

14. A pharmaceutical composition comprising the sulfonamide derivative of claim 1 and a pharmaceutically acceptable carrier, diluent, or excipient.

15. The pharmaceutical composition of claim 14, wherein the sulfonamide derivative has R of 4-hydroxy-L-proline methyl ester.

* * * * *